(12) United States Patent
Trabada et al.

(10) Patent No.: US 8,460,334 B2
(45) Date of Patent: Jun. 11, 2013

(54) ENDOLUMINAL ACCESS DEVICES AND RELATED METHODS OF USE

(75) Inventors: German Trabada, Pembroke Pines, FL (US); Russell F. Durgin, Jr., Attleboro, MA (US); Robert Sakal, Bolton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1828 days.

(21) Appl. No.: 11/644,384

(22) Filed: Dec. 21, 2006
(Under 37 CFR 1.47)

(65) Prior Publication Data

US 2007/0265547 A1 Nov. 15, 2007

Related U.S. Application Data

(62) Division of application No. 10/753,848, filed on Jan. 8, 2004.

(51) Int. Cl.
*A61M 29/00* (2006.01)
*A61B 17/32* (2006.01)
*A61B 17/22* (2006.01)

(52) U.S. Cl.
USPC ............................ 606/194; 606/167; 606/159

(58) Field of Classification Search
USPC ...... 604/95.1, 156, 157, 528, 95.03; 600/585, 600/101, 117, 118, 115; 606/190, 191, 193, 606/108, 139, 142, 157, 151, 130
See application file for complete search history.

(56) References Cited

U.S. PATENT DOCUMENTS

| | | | |
|---|---|---|---|
| 6,238,401 B1 | 5/2001 | Richter | |
| 6,971,990 B2 * | 12/2005 | Ziegler et al. | 600/114 |
| 7,229,401 B2 * | 6/2007 | Kindlein | 600/7 |
| 2002/0065523 A1 * | 5/2002 | McAlister et al. | 606/139 |

FOREIGN PATENT DOCUMENTS

| | | | |
|---|---|---|---|
| EP | 976417 A1 * | 2/2000 | |
| JP | 2000-051366 | 2/2000 | |

* cited by examiner

*Primary Examiner* — Tuan V Nguyen
(74) *Attorney, Agent, or Firm* — Fay Kaplun & Marcin, LLP

(57) ABSTRACT

A modular device for tissue resection includes a housing, a motor, a tissue receiving chamber, a grabbing mechanism and a resection mechanism. The housing includes a guide track receiving lumen extending therethrough. The motor is mounted within the housing. The motor is selectively engageable with a guide track received within the guide track lumen to move the modular device therealong. The tissue receiving chamber is formed within the housing. The grabbing mechanism draws a selected portion of tissue into the tissue receiving chamber. The resection mechanism resects the selected portion of tissue.

8 Claims, 10 Drawing Sheets

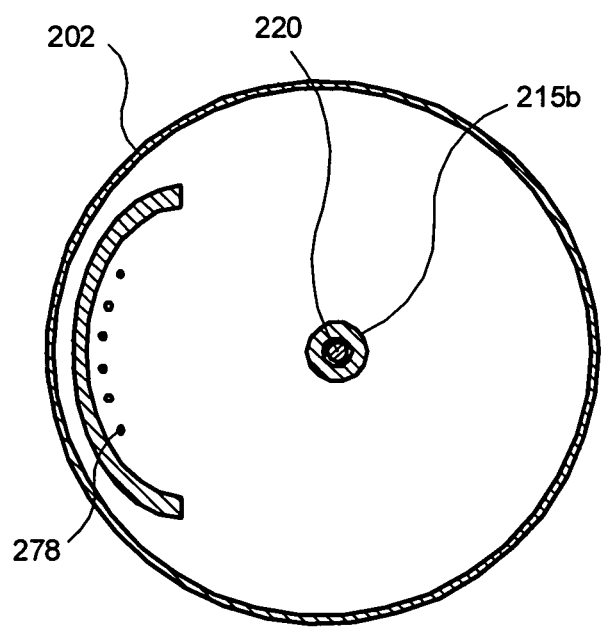
F I G. 8B ic ENDOLUMINAL ACCESS DEVICES AND
RELATED METHODS OF USE

PRIORITY CLAIM

This application is a Divisional application of U.S. patent application Ser. No. 10/753,848 filed Jan. 8, 2004 entitled "Endoluminal Access Devices and Related Methods of Use". The entire disclosure of the prior application is considered as being part of the disclosure of the accompanying application and hereby expressly incorporated by reference herein

FIELD OF THE INVENTION

The present invention relates to the field of endoluminal access devices, and more particularly to endoluminal access devices driven by mechanical, electrical, and other like devices, and related methods of using such devices.

BACKGROUND OF THE INVENTION

Many endoluminal procedures are performed each year. Endoluminal procedures take place within tubes or lumens of the human body, such as vascular, gastrointestinal, or air exchange lumens, and generally involve the diagnosis and/or treatment of diseases and/or debilitating conditions. Endoluminal procedures generally involve use of a rigid or flexible tube such as an endoscope, which may be introduced into the human body through a body orifice, such as the mouth or rectum or through an incision. Endoscopes allow users to view intended internal treatment sites and may provide one or more working channels, or pathways, to the treatment site.

Endoscopes may be manually steered or positioned through the body until the endoscope is properly positioned. For some devices used to remove tumors and polyps, e.g., full thickness resection devices (FTRDs), accurate positioning is important to successful use.

SUMMARY OF THE INVENTION

The present invention relates to a modular device for tissue resection includes a housing, a motor, a tissue receiving chamber, a grabbing mechanism and a resection mechanism. The housing includes a guide track receiving lumen extending therethrough. The motor is mounted within the housing. The motor is selectively engageable with a guide track received within the guide track lumen to move the modular device therealong. The tissue receiving chamber is formed within the housing. The grabbing mechanism draws a selected portion of tissue into the tissue receiving chamber. The resection mechanism resects the selected portion of tissue.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

FIG. 8B is a cross-section of the distal portion of the modular device of FIG. 7A taken at line B-B of FIG. 8A.

DETAILED DESCRIPTION

Reference will now be made in detail to the present exemplary embodiments of the invention, examples of which are illustrated in the accompanying drawings. Wherever possible, the same reference numbers will be used throughout the drawings to refer to the same or like parts.

According to the present invention, an endoluminal access system includes a modular device containing tools for performing an internal procedure or treatment. The modular device may be moved within a body lumen, for example, along a guidewire inserted thereinto without an endoscope. The modular device may optionally include an internal or an external power source driving the modular device along the guidewire.

The use of a guidewire to direct the device to the treatment site rather than an endoscope may make access to internal treatment sites less time consuming and may reduce trauma to the body tissues associated with the insertion of an endoscope. A guidewire may be inserted into the body lumen and directed to the treatment site by methods known in the art. The modular device may then be slidably coupled to the guidewire and moved therealong to the treatment site. If the modular device is coupled to a powered drive mechanism, there will be no need for an operator to push or force the modular device into the body lumen. Body tissues/lumens may be required give way as the modular device moves along the guidewire. However, these tissue do not remain in a stretched or expanded state as long as is required for an endoscope which will extend along the entire distance from the point at which the endoscope enters the body to the treatment site. In contrast, only that portion of the tissue currently in contact with the modular device may be impacted while the rest of the tissue between the treatment site and the opening to the body lumen will be occupied only by the small diameter guide wire. Thus, trauma to surrounding tissue may be reduced. In addition, depending on the number and nature of the tools required for a certain procedure, the modular device employed may be smaller in diameter than a standard endoscope. This may further reduce trauma to surrounding tissue.

In addition, as described below, the driving mechanism of the modular device and an optional viewing device, make it is possible to accurately position the modular device. The accuracy in positioning may reduce the time required for the treatment and may also reduce risk of erroneously treating the wrong area.

Figure 1:
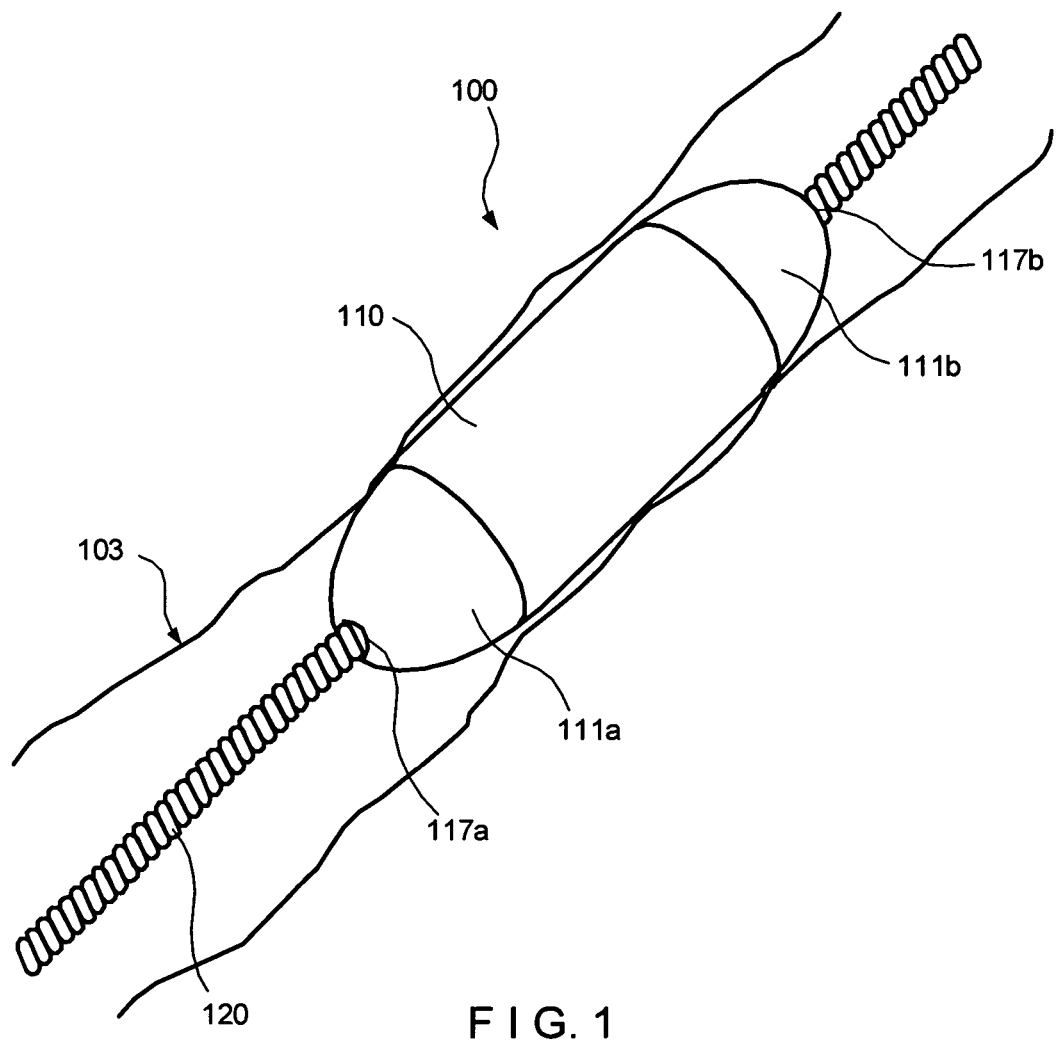
FIG. 1 is a perspective view of an access device according to an embodiment of the present invention.

According to the present invention and as embodied in FIG. 1, an endoluminal modular access system 100 is provided. System 100 may generally include a modular device 110, a track 120 for guiding/moving the modular device 110, and a drive mechanism 112 for driving the modular device 110 along the track 120. Each of these general portions of system 100 will be described in detail below.

As embodied herein and shown in FIG. 1, a modular device 110 for traveling within a body lumen 103 may vary in size and shape dependent upon the size and type of tools required for a given procedure and contained therewithin and/or the size and shape of the body lumen in which it is to be used. The exterior of modular device 110 may optionally include a hydrophilic coating to facilitate passage through the body lumen 103 and may preferably have rounded edges to facilitate movement within the body lumen 103. Modular device 110 also includes holes 117a, 117b formed in the proximal and distal ends, respectively, of the modular device 110 for receiving the guide track 120 as described in detail below.

Figure 2:
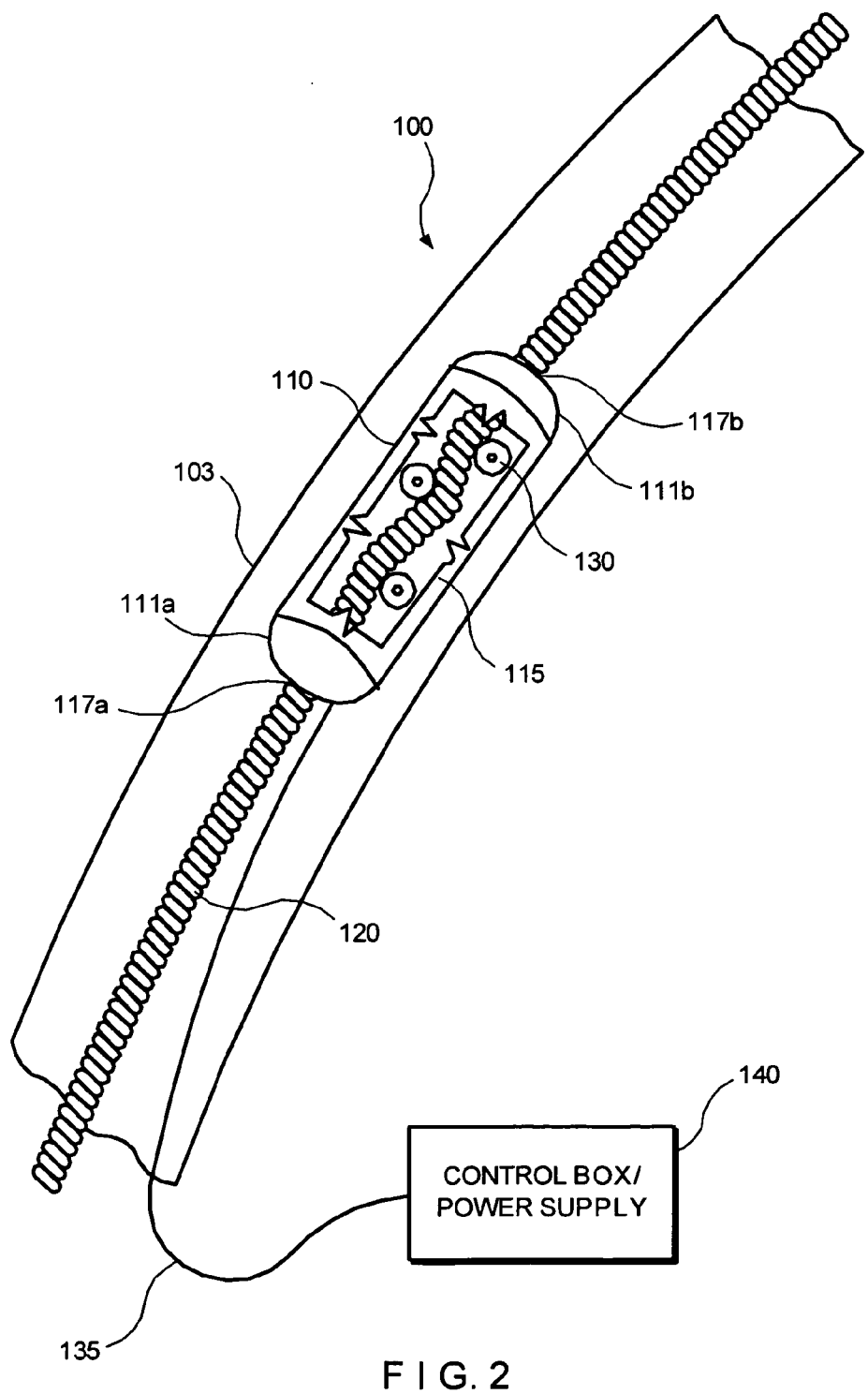
FIG. 2 is a partial cross-section view of the access device of FIG. 1.

FIG. 2 shows an embodiment of a drive mechanism 112 which may be provided in modular device 110. As shown in FIG. 2, the drive mechanism 112 includes a motor 115 engaging a guide track 120. Motor 115 is contained within modular device 110 and may be connected via a cable 135 to an external power source and control box 140. Cable 135 extends from modular device 110 to the power source and control box 140 which is located externally of the patient. In this embodiment, motor 115 is connected to gear wheels 130 so that gear wheels 130 rotate when powered by the motor 115. Control box 140 enables a user to determine a direction of rotation of gear wheels 130 and may also allow a user to control a speed of rotation thereof. When rotated in a first direction, gear wheels 130 draw the modular device 110 distally along the guide track 120 into the lumen of the body of the patient and away from the operator. When rotated in the second direction, the gear wheels 130 draw the modular device 110 proximally along the guide track 120 toward the external opening of the lumen of the patient and toward the operator.

Those skilled in the art will understand that various known suitable sources of power and various known suitable devices for controlling the source of power, movement and operation of the modular device 110 may be employed. For example, the power source may be a battery device, or a source of air or hydraulic pressure such as a pneumatic or hydraulic pump. In addition, although FIG. 2 shows the use of three gear wheels 130, those skilled in the art will understand that any suitable number and type of gear wheels or other like device may be employed to grip track 120 and move the modular device 110 therealong. For example, a continuous belt may frictionally engage the guide track 120 so that rotation of the belt drives the modular device 110 therealong. The invention is not to be limited to any particular power supply or controller, or drive mechanism type.

As embodied herein and shown in FIGS. 1 and 2, modular device 110 moves along a guide track 120. Guide track 120 may be, for example, a straight guidewire or shaft, a catheter, a coiled guidewire or metal shaft, or any like device. Guide track 120 is intended to be inserted into the lumen 103 of the patient toward the desired treatment site prior to the insertion of the modular device 110 using known techniques. The guide track 120 may then optionally be anchored within the lumen at a desired location relative to the treatment site. A proximal end of the guide track 120 is then inserted into the hole 117b and the modular device 110 is driven distally along the guide track 120 until the proximal end of the guide track 120 exits the hole 117a. Further advancing the modular device 110 distally along the guide track 120, the operator then guides the modular device 110 into the opening to the body lumen and advances the modular device 110 distally to the treatment site.

In the embodiment shown in FIG. 2, gear wheels 130 engage guide track 120, which may be formed, for example, as a straight guidewire or flexible shaft. Gear wheels 130 are powered by the motor 115 which is powered by the external power supply. If a forward direction is selected on the control box, the gear wheels 130 will rotate and grip track 120 such that modular device 110 moves in a forward, distal direction along track 120. If a reverse direction is selected, the modular device 110 moves in a rearward, proximal direction along track 120. In addition to direction control, control of the speed of the modular device 110 may be provided so that, for example, modular device 110 can be more quickly moved to the treatment site, and have its position fine-tuned at lesser speeds. The speed of modular device 110 may be dictated by considerations of safety to the patient and the capability of the power source and drive device.

Figure 3:
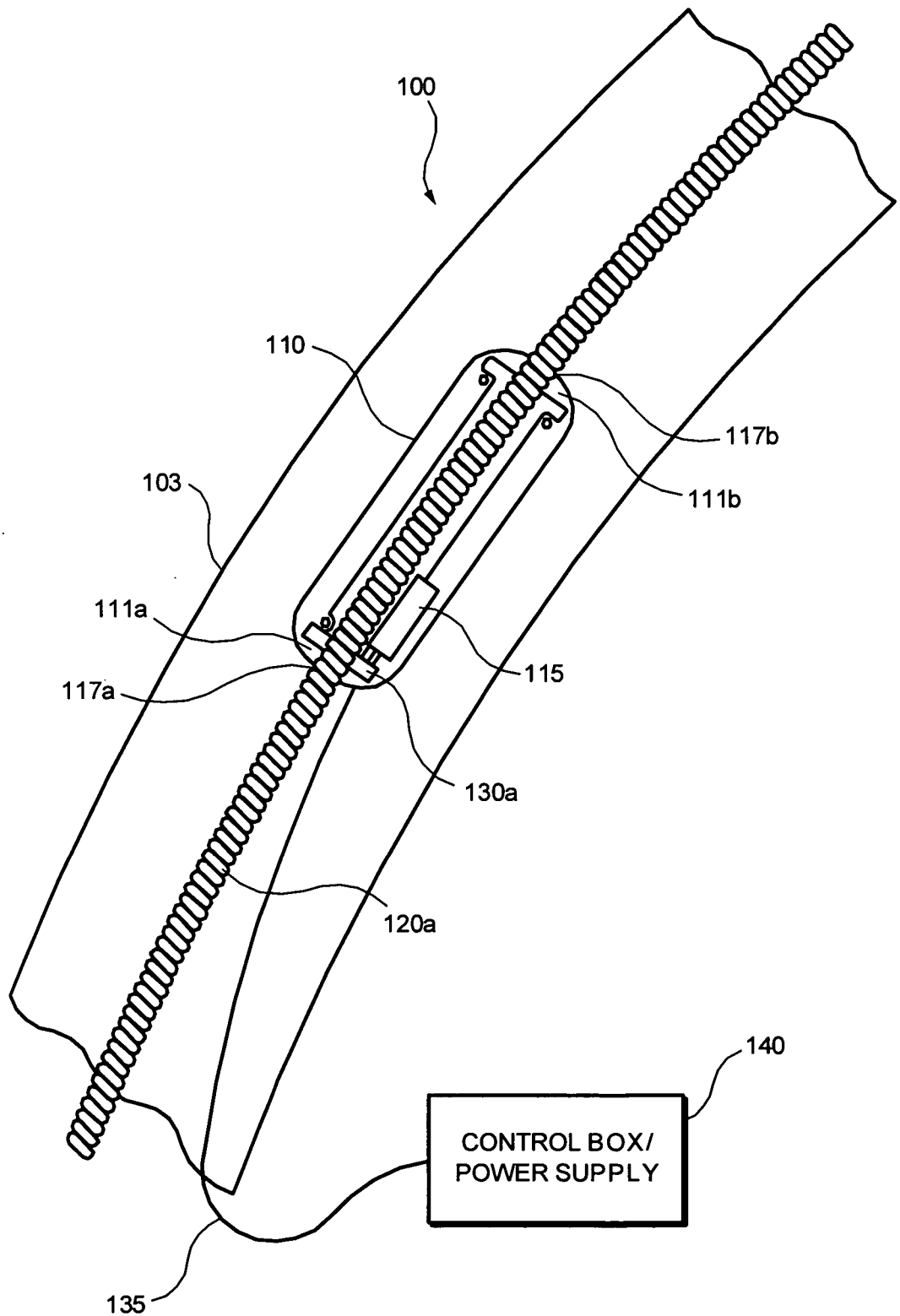
FIG. 3 is a cross-section view of another embodiment of an access device according to the present invention.

FIG. 3 shows another embodiment of a drive mechanism 112 provided in modular device 110. In this embodiment, an electric motor 115 is again provided inside modular device 110. Those skilled in the art will understand that the motors employed in connection with any of the embodiments of this invention need not be electric motors. Alternatively, as would be understood by those of skill in the art, the functions of all of these motors may be provided by fluid powered motors such as air/hydraulic motors. Such motors may be run in two directions by, for example, including two separate fluid supply lines, one of which is to be engaged for a first direction of rotation of the motor with engagement of the second operating the motor in the opposite direction. Motor 115 is powered as described above, and is connected to a gear set 130a. Gear set 130a is positioned within modular device 110 to engage guide track 120a, which is embodied as a coiled guidewire or shaft. At least one portion of modular device 110 which contacts and sits on guide track 120a includes a threaded portion to allow modular device 110 to move along coiled guide track 120a. The threaded portion is preferably a threaded hole 117b in an end of modular device 110 which intermeshes with the coils of track 120a. Gear set 130a engages the coiled guide track 120a, and when powered, gear set 130a moves along the coils of guide track 120a to move modular device 110 in either a forward (distal) or reverse (proximal) direction.

Figure 4:
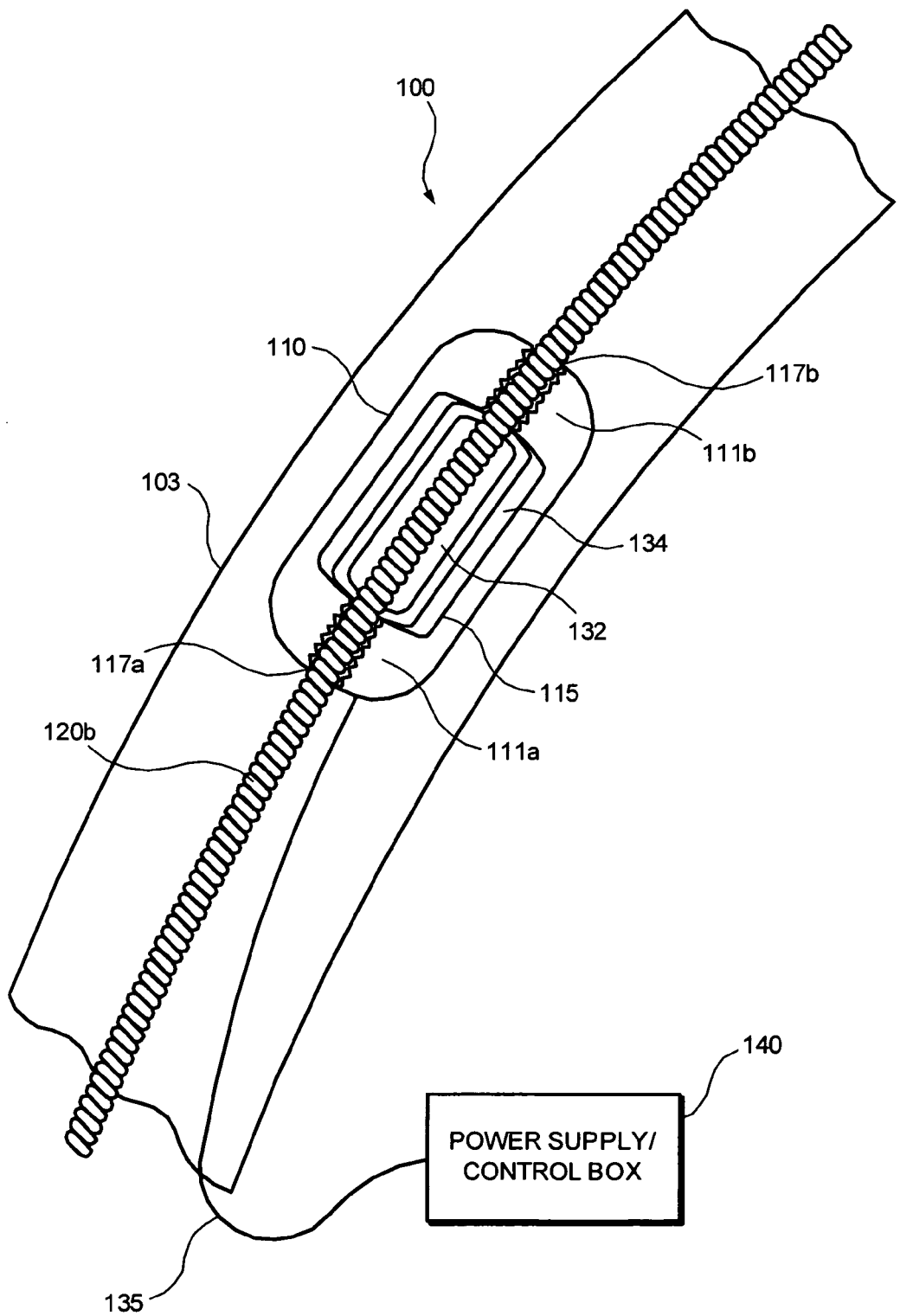
FIG. 4 is a cross-section view of a further embodiment of an access device according to the present invention.

FIG. 4 shows a further embodiment of a drive mechanism 112 provided in modular device 110. In this embodiment, an electric motor 115 is provided inside modular device 110. The motor 115 may be powered as described above, and includes a rotor 132 and stator 134 arrangement, as would be understood by those of skill in the art. The rotor 132 is positioned within the stator portion 134 and includes a central threaded portion. Rotor 132 is positioned within the modular device 110 to engage and rotate about guide track 120b, which is embodied as a coiled guidewire or shaft. As shown in FIG. 4, the coils of the guide track 120b provide a substantially helical threaded surface which is engaged by the corresponding threaded portions 111a, 111b of the lumen extending through the modular device 110 through which the guide track 120b passes are formed at the proximal and distal ends of the modular device 110. Contact between these threaded potions 111a, 111b and the guide track 120b as the modular device 110 is rotated by the electric motor 115 moves the modular device proximally or distally therealong depending on the direction of rotation. Those skilled in the art will understand that the rotor 132 may optionally be nonrotatably coupled to the threaded portions 111a, 111b while a radially outer portion of the modular device 110 is rotatably coupled to the rotor 132 and the threaded portions 111a, 111b so that this radially outer portion may maintain a substantially constant angular orientation relative to the guide track 120b as the modular device 110 is moved therealong.

Furthermore, as shown in FIGS. 5A-5D, the endoluminal modular access system 100 may also include an anchor module 150 to anchor a portion of the guide track 120b (e.g., the distal end thereof) at a desired location within the body lumen 103 so that the modular device can be more easily advanced along guide track 120b. The anchor module 150 may preferably contain a motor (e.g., a servo screw motor) (not shown) which, when powered, moves the anchor module 150 along the guide track 120b in a manner similar to that described in regard to the motion of the modular device 110 along the guide track 120. Furthermore, those skilled in the art will understand that any suitable motor or other like drive device may be used to power the anchor module 150. For example, the anchor module 150 may utilize any of the drive devices and activators described in connection with the modular devices 110 of this invention. The anchor module 150 preferably has rounded edges to minimize trauma to body tissue and to ease movement of the anchor module 150 through the body lumen. An anchoring extendible member 152 is provided on the anchor module 150 which may be configured in a first radially compressed state for insertion and retraction from the patient's body and a second radially expanded state in which the extendible member 152 contacts the wall of the body lumen 103 to anchor itself and the guide track 120 in place. Those skilled in the art will understand that the expandable member may be an extendible cage or arm or, as shown in FIGS. 5A-5D, a balloon. Furthermore, those of skill in the art will understand that the anchoring module 140 may include more than one extendible member 152 to aid in stabilizing the anchor the module 150 in position. In use, the anchor module 150 is preferably deployed when the distal end of the guide track 120 is brought to the desired location within the body lumen 103 prior to the insertion of the modular device 110 into the body lumen. The motor within the anchor module 150 may engage the guide track 120b in any manner similar to those described in regard to the modular device 110 (e.g., a gear or belt drive, threaded holes engaging a helical thread of the guide track 120, etc.).

Once at the distal end of the track 120b has reached the desired location within the body lumen 103, the extendible member 152, is actuated. For example, for a balloon extendible member 152, the operator supplies fluid to the balloon via the tube 156 to expand the balloon until it contacts the wall of the body lumen 103. To do this, the operator connects the tube 156 to a suitable source of fluid preferably external to the patient's body. The balloon of extendible member 152 expands until it contacts and pushes against the walls of the body lumen. Thus, extendible member 152 anchors itself within the body lumen and because it is anchored, it stabilizes the track 120b for the modular device 110.

Figure 5A:
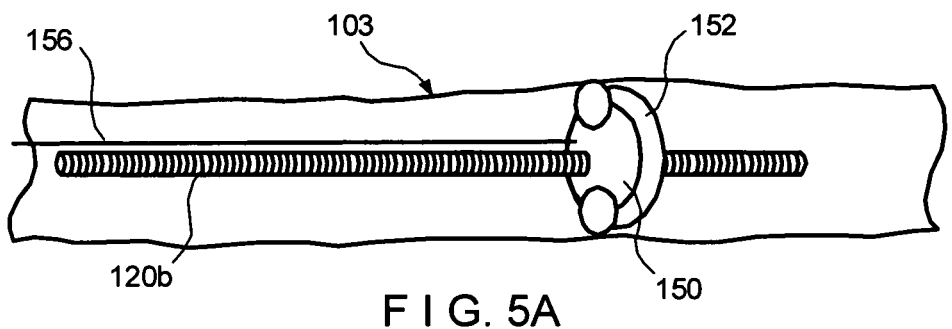
FIG. 5A is a side view of a still further embodiment of an access device of the present invention in a first configuration.
Figure 5B:
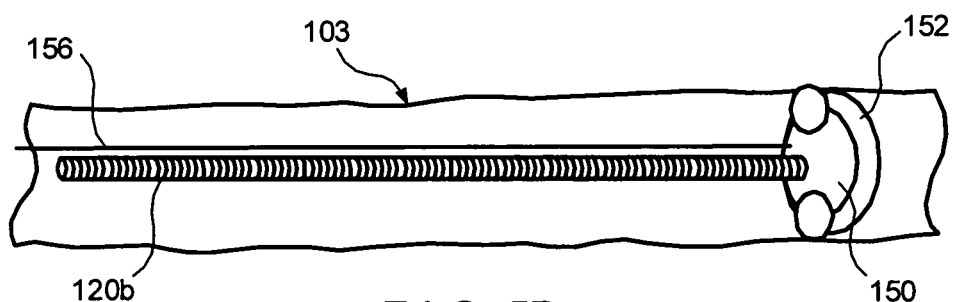
FIG. 5B is a side view of the device of FIG. 5A in a second configuration.
Figure 5C:
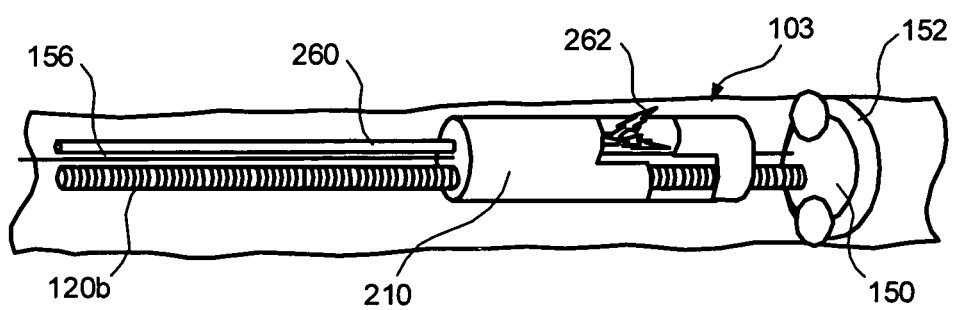
FIG. 5C is a side view of the device of FIG. 5A in a third configuration.
Figure 5D:
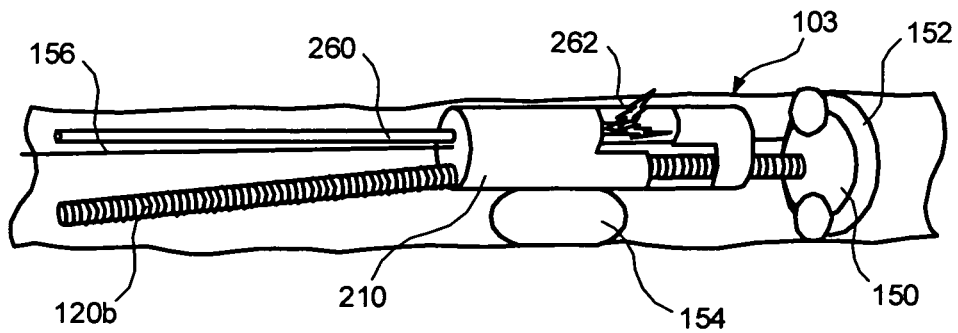
FIG. 5D is a side view of the device of FIG. 5A in a fourth configuration.

In this preferred embodiment as shown in FIG. 5D, the modular device 110 may also include an extendible member 154, (e.g., a positioning balloon) for stabilizing the position of the module device 110 during the procedure to enable optimal use of the tools contained therein. The extendible member 154 may be arranged such that, when in the extended configuration, pushes the modular device 110 into contact with one side of the lumen 103 (e.g., the side of the lumen on which the tissue to be treated is located). The extendible member 154 is supplied with an inflation fluid (e.g., air or saline) via an inflation lumen (not shown) which is preferably separate from that used to inflate from the tube 156 which is used to inflate the balloon extendible member 152.

In a further embodiment of an endoluminal modular access system, the modular device 210 may be a full thickness resection device (FTRD). The function of an FTRD is to remove a full thickness section of tissue from an organ and reseal the opening created through the resection. The FTRD modular device 210 is shown in FIGS. 5C and 5D and FIGS. 7 and 8.

Figure 7A:
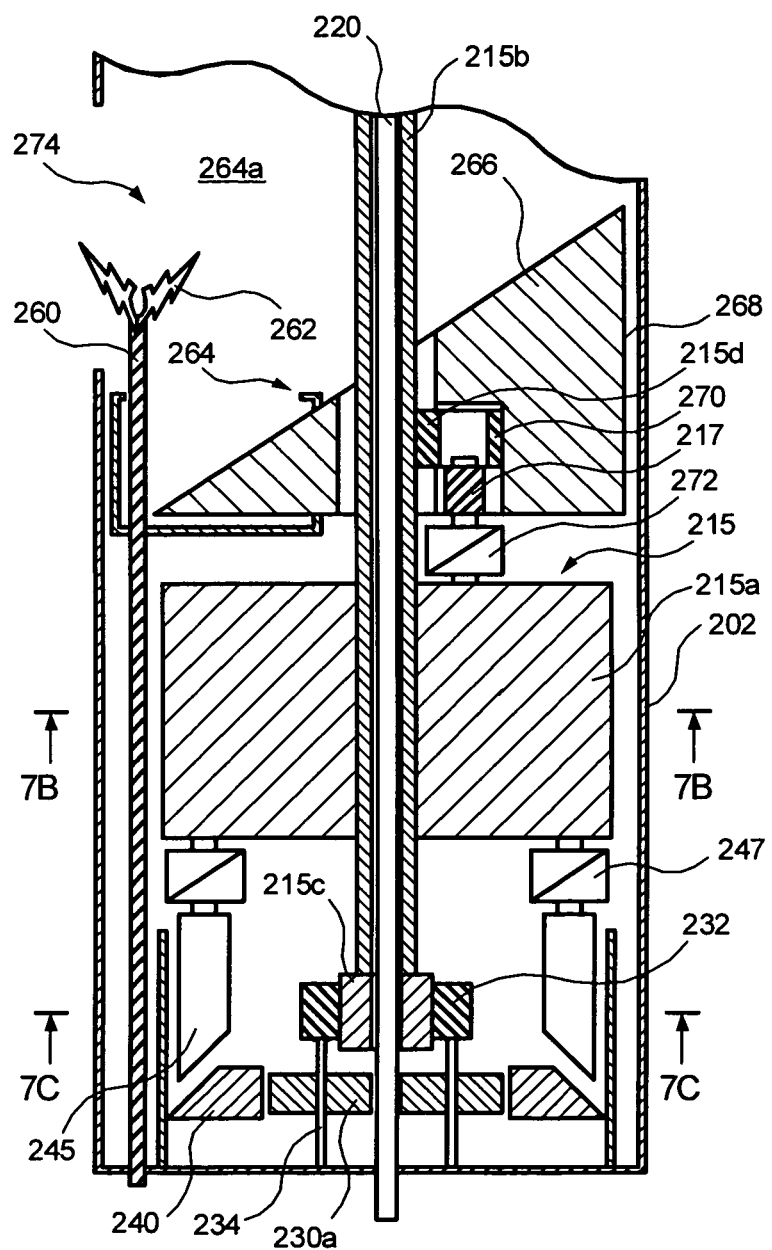
FIG. 7A is a cross-section view of a proximal portion of a modular device for use in the access device of FIGS. 5A-5D.
Figure 7B:
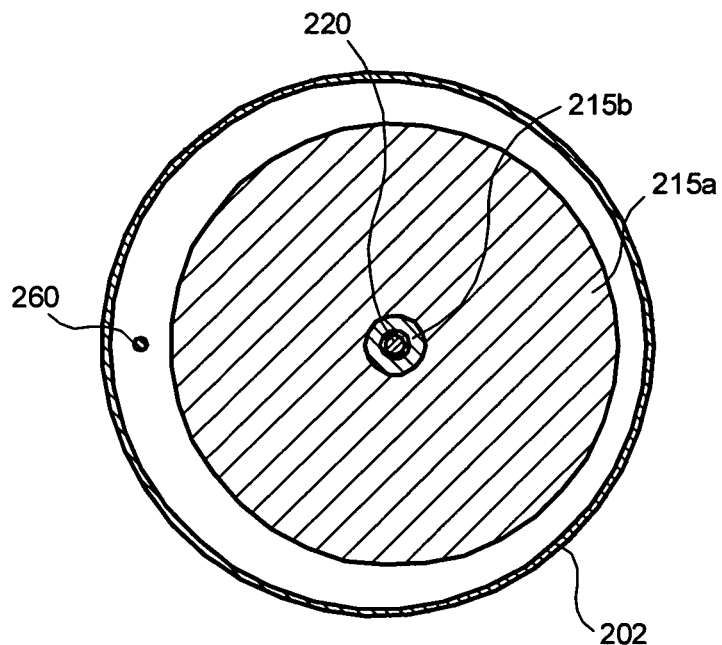
FIG. 7B is a cross-section view of a proximal portion of the modular device of FIG. 7A taken at line B-B of FIG. 7A.
Figure 7C:
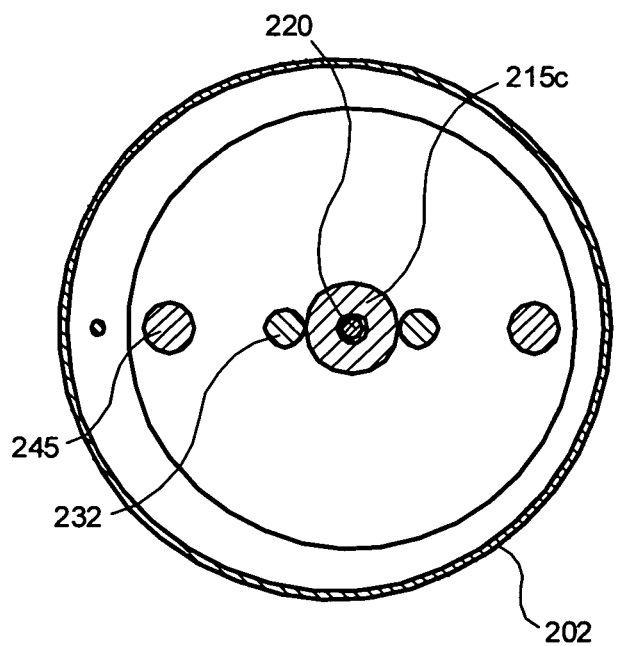
FIG. 7C is a cross-section view of the proximal portion of the modular device of FIG. 7 taken at line C-C of FIG. 7A.

FIG. 7A shows a cross-section of a proximal portion of the FTRD modular device 210. As can be seen in FIG. 7A, FTRD modular device 210 includes an outer casing 202, and a central motor 215. Outer casing 202 is preferably smooth, and formed of a biocompatible material such as a biocompatible plastic or metal, as would be understood by those of skill in the art. Furthermore, the outer casing 202 may include a hydrophilic coating. The outer casing 202 is preferably oval or circular in cross-section with blunt, rounded ends. Other shapes such as, for example, a rectangular cross-section with rounded corners may also be used. The size of the outer casing 202 is preferably between 2 and 10 cm in length with a circumference (or perimeter) of between 3 and 19 cm. As would be understood by those of skill in the art, the size of the outer casing 202 may vary based upon the type and size of the tools required for a particular procedure and which are contained within the outer casing 202. Motor 215 may preferably be a direct current electric motor which may be driven in two directions. Motor 215 includes outer windings 215a which are stationary and attached to outer casing 202 and an armature formed as a sleeve 215b having a central lumen extending therethrough. A guide track, e.g., in the form of a catheter 220 may be slidably received in the central lumen of the armature sleeve 215b with the armature sleeve 215b rotating thereabout when the motor 215 is driven to move the FTRD modular device 210 along the catheter 220 via the drive mechanism described below.

Figure 8A:
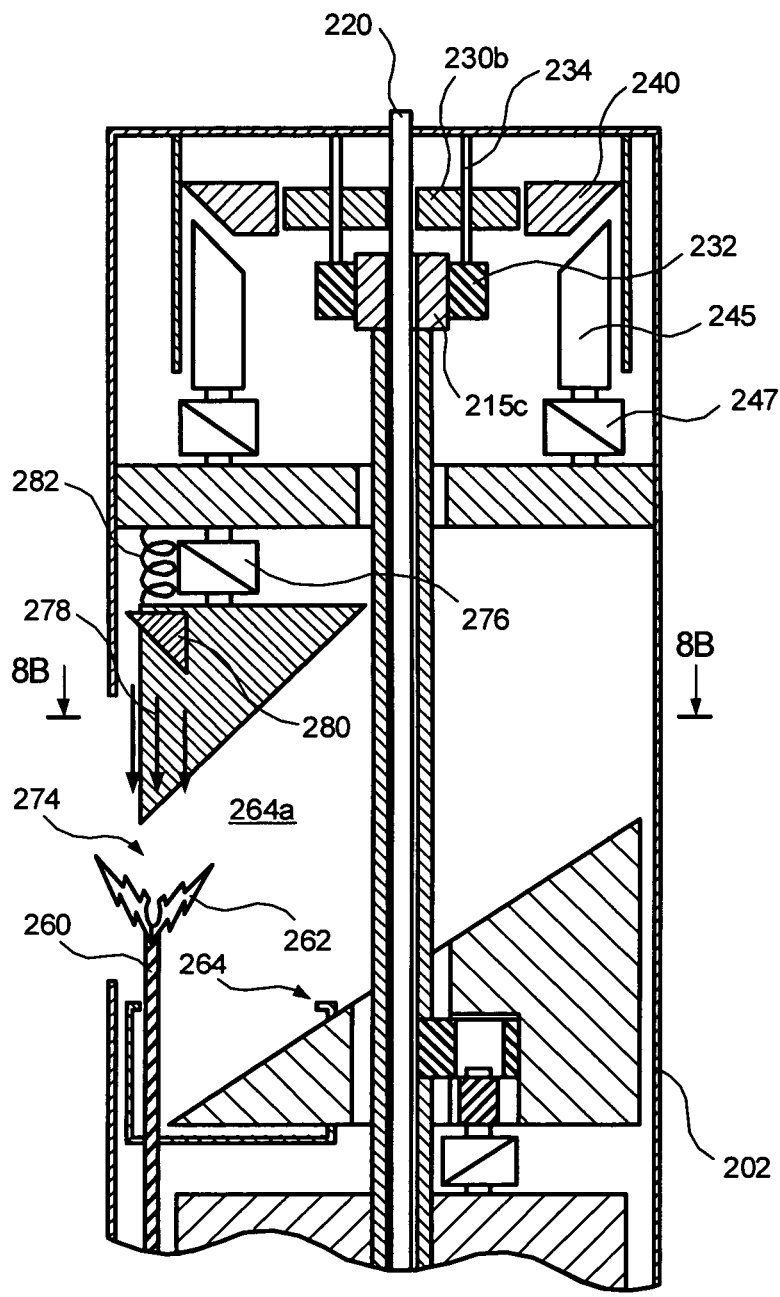
FIG. 8A is a cross-section view of a distal portion of the modular device of FIG. 7A.

As shown in FIGS. 7A and 8A, the drive mechanism 112 provided in the FTRD modular device 210 includes proximal and distal sets of roller gears 230a, 230b positioned around the catheter 220 proximally and distally of the armature sleeve 215b, respectively. When in an unpowered state, roller gears 230a, 230b are moved out of engagement with the catheter 220. However, when power is supplied to the motor 215, the roller gears 230a, 230b are firmly pressed against the catheter 220 to engage catheter 220 so that rotation of the roller gears 230a and 230b draws the FTRD modular device 210 along the catheter 220 either distally or proximally, depending on a direction of rotation of the motor 215.

Roller gears 230a, 230b are powered by armature sleeve 215b through armature sleeve gear 215c and roller takeoff gear 232. Roller takeoff gear 232 is connected to roller gears 230a, 230b through a shaft 234. Roller gears 230a, 230b are moved into and out of contact with the catheter 220 by pressers 240 which are moved radially inward when the motor 215 is powered contact the roller gears 230a, 230b to press the roller gears 230a, 230b into contact with the catheter 220. When power is withdrawn from the motor 215, the pressers 240 are moved radially outward to remove the inward pressure on the roller gears 230a, 230b. The roller gears 230a, 230b are biased radially outward by a biasing member (not shown) so that, when the pressers 240 are moved out of contact therewith, the roller gears 230a, 230b are automatically withdrawn from contact with the catheter 220. Pressers 240 are shifted radially by longitudinal pressers 245 which are moved longitudinally into and out of contact with the pressers 240 by an electrically powered linear transducer 247. As would be understood by those of skill in the art, transducer 247 may be an electrically charged magnetic solenoid configured to apply linear force to the longitudinal pressers 245. Alternatively, transducer 247 may be replaced by a hydraulic piston.

As embodied herein and shown in FIGS. 7A and 8A, FTRD modular device 210 includes a grabbing element 260 having end grippers 262 for grabbing a selected tissue sample and pull the tissue into a tissue receiving chamber 264a formed within the FTRD modular device 210. Grabbing element 260 is mechanically controlled by manipulation of an actuator which remains external to the patient and which is connected to a proximal end of grabbing element 260 by, for example, a control cable, flexible drive shaft, hydraulic line, as would be understood by those of skill in the art. Furthermore, any of various known suitable actuators may be used to allow the operator to control the grabbing element 260. In an alternative embodiment, grabbing element 260 may be replaced with a vacuum grabber for drawing the selected tissue into the tissue receiving chamber 264a as would be understood by those of skill in the art.

As embodied herein and shown in FIGS. 7A and 8A, a cutting element 266, which may, for example, be in the form of a curved blade having a cutting surface extending at an angle relative to a longitudinal axis the FTRD modular device 210, in an operative configuration extends into the tissue receiving chamber 264a. Cutting element 266 is operated after the selected portion of tissue has been stapled as described below to cut the selected portion of tissue away from the body lumen so that it may be retained within the tissue receiving chamber 264a. A linear transducer 272 engages and disengages a cutter engaging element 270. After FTRD modular device 210 has reached a desired position, the actuator 247 is released to disengage roller gears 230a, 230b thereby preventing further movement of the FTRD modular device 210 along the catheter 220.

A window formed in the outer casing 202 is covered by clamping element 274. The window may then be opened, as shown in FIG. 8A, by activating a linear transducer 276 which is coupled to the clamping element 274. The linear transducer 276 may be controlled by, for example, an electric solenoid or fluid powered cylinder as would be understood by those of skill in the art. A selected portion of the tissue is drawn into the tissue receiving chamber 264a using the grabbing element 260 and operator controls the linear transducer 276 to move the clamping element 274 into the closed position adjacent the anvil 264 to close the window and clamp the tissue between the anvil 264 and the clamping element 274. The anvil 264 is driven by a hammer 280 to form the staples, as described below to staple to tissue, as described below and, after this stapling has been completed, the actuator 272 is powered and a drive train is established between drive gears 215D, an idler gear 217 on the end of actuator 272, and cutter gear 270 to begin movement of the cutting element 266 to sever the tissue radially within the stapled tissue. As the connection between the roller gears 230a, 230b has been removed, the motor 215 may be driven to actuate the cutting element 266 without driving the FTRD modular device along the catheter 220.

When linear transducer 272 engages the cutter engaging element 270, a cutter sleeve armature gear 215D is activated by cutter engaging element 270. Cutter sleeve armature gear 215D, in turn, causes rotation of a cutter take up gear 268 which rotates cutting element 266, causing it to cut the selected tissue sample. Structural members extend between the transducers 247, 276 to support them and the tissue receiving chamber 264a extends between an anvil 264 (which forms staples) and the clamping element 274.

Also provided in FTRD modular device 210 is a stapler hammer 280. Stapler hammer 280 inserts staples 278 into the clamped tissue. Stapler hammer 280 is spring loaded and actuated by manual release of the spring 282. A manual release trigger is controlled by the operator through manipulation of an actuator external to the patient to actuate the stapler hammer 280 to insert staples 278 into the tissue. Spring 282 may be actuated, for example, when released via a mechanical cable from a compressed state. As would be understood by those of skill in the art, although element 282 is shown as a spring, other devices such as the actuators previously described may be used. Alternatively, instead of or in addition to the FTRD modular device 210, other devices such as cutters, tissue cauterizing devices, graspers, biopsy devices, etc., may be contained within the modular device 210. Additionally, the device may be actuated by other means such as remote control or under computer control.

A preferred method of using an endoluminal modular access device according to one embodiment of the present invention will now be described with reference to FIGS. 5A-5D. First, a guide track 120b is selected and inserted by the operator into a body lumen 103 of the patient's body. Selection of an appropriate guide track 120b may depend on the size and characteristics of the body lumen, the corresponding size of the modular device 110, the types of tools contained within the modular device 110 and/or required for the particular procedure to be performed and which would effect the weight of the modular device 110, and the characteristics of the power source being used to drive the modular device 110 along the track 120b. After the guide track 120b has been inserted into the modular device 110, a distal end of the guide track 120b is advanced to the treatment site and anchored to a desired location at or near the treatment site as would be understood by those of skill in the art. For example, an anchor module 150 may be placed on the guide track 120b and advanced by actuation of, for example, a servo screw motor within the anchor module 150. The anchor module 150 may then be advanced to the distal end of the guide track 120b and, at this point, an extendible member 152 is expanded, e.g, by supplying inflation fluid to a tube 156 to inflate an anchoring balloon of the extendible member 152 thereby anchoring the guide track 120b at the desired position within the body lumen 103. Those skilled in the art will understand that the modular device 110 need not be coupled to the guide track 120b before the distal end thereof is anchored at the desired location. Alternatively, after the distal end of the guide track 120b has been anchored in place, the modular device 110 may be advanced over the proximal end of the guide track 120b into the body lumen 103.

Once guide track 120b has been anchored within body lumen 103, modular device 110 is attached to guide track 120b at the proximal end of guide track 120b external to the patient. Modular device 110 is then advanced along guide track 120b toward the distal end thereof and is positioned within the body lumen 103. If desired, when the device has reached a desired position within the body lumen 103, the extendible member 154 may be deployed by an operator, e.g., by introducing fluid to the tube 156 which extends to the extendible member 154, in order to push modular device 110 into a position adjacent the wall of lumen 103.

For example, in the case of the FTRD modular device 210, a window is provided in the outer casing 202 of FTRD modular device 210 through which a grabbing element 260 and grippers 262 may be extended to grab and retrieve a selected portion of tissue when the clamping element 274 has been moved to an open position away from the window. The selected tissue sample is then pulled into the tissue receiving chamber 264a (i.e., the space between the anvil 264 and the clamping element 274). As described above, once the selected tissue sample has been drawn into the tissue receiving chamber 264a, the actuator 276 is operated to move the clamping element 274 into the closed position clamping the tissue against the anvil 264. When clamped into the tissue receiving chamber 264a, the selected portion of tissue should be folded over so that a portion of tissue twice the thickness of the organ is clamped between the clamping element 274 and the anvil 264 (i.e., the clamping element 274 contacts an inner surface of a first portion of the wall of the organ with an outer surface of the first portion of the organ contacting an outer surface of a second portion of the organ and an inner surface of the second portion of the organ contacts the anvil 264. The gripper 262 may then be released and withdrawn. The hammer 280 is then operated to drive staples through the full thickness of the tissue of the first and second portions of the organ with the staples being formed against the anvil 264. After completing the stapling, the cutter element 266 is actuated and begins rotating through the selected portion of tissue to cut this tissue from the wall of the body lumen 103. Because the full thickness of the tissue of the first and second portions of the organ has been stapled together, cutting away that portion of tissue received radially within the stapled portion leaves the organ sealed. After the cutting has been completed, the extendible member 154 is deflated, and the FTRD modular device 210 is driven in reverse (i.e., proximally) along guide track 120b toward the external opening of the lumen. When the FTRD modular device 210 has been removed from the body lumen 103, the extendible member 152 is deflated, and the anchor module 150 is also driven along guide track 120b proximally to the external opening of the body lumen 103. Once the extendible member 152 has been removed from the body lumen 103, the guide track 120b is withdrawn therefrom by the operator, and if necessary, the external opening to the body lumen 103 is surgically closed.

Figure 6A:
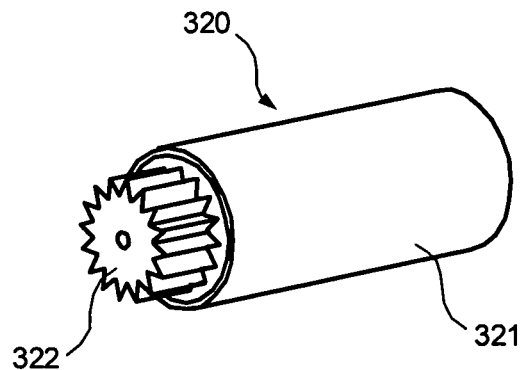
FIG. 6A is a perspective view of an external drive shaft according to an embodiment of the present invention.
Figure 6B:
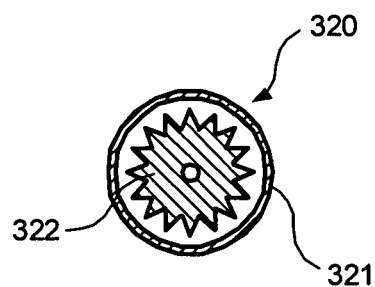
FIG. 6B is a cross-section view of the drive shaft of FIG. 6A.
Figure 6C:
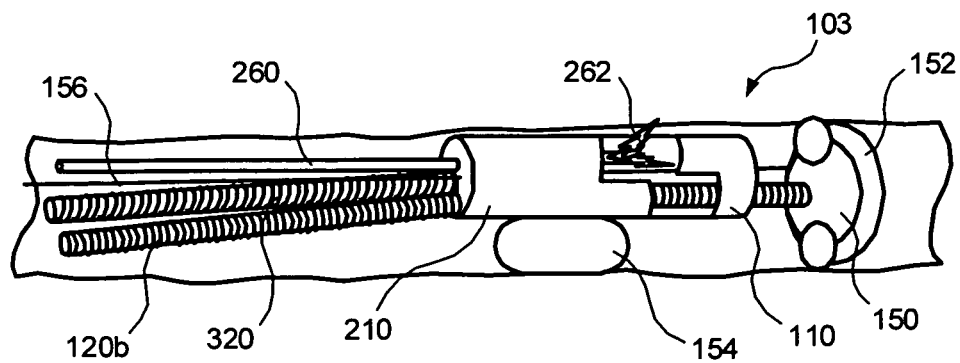
FIG. 6C shows a side view of an additional embodiment of an access device according to the present invention including a drive shaft as shown in FIGS. 6A and 6B.

Alternatively, as shown in FIGS. 6A, 6B and 6C and described further herein, an alternate drive mechanism including a drive shaft 320 which extends from the modular device 110 through the body lumen and out of the body where it may be coupled to a power source (not shown). Those skilled in the art will understand that the modular device 110 according to this embodiment may be substantially similar to those of the previously described embodiments, except that no motor or other power source is located therewithin. Rather, motive power is transmitted to the modular device from the external power source via the drive shaft 320. The drive shaft 320 extends into the modular and couples to a drive mechanism (not shown) which may be constructed in accord with any of the previously described embodiments. Specifically, the drive shaft 320 includes a thick outer shell 321 with an inner gear 322 being rotatable within the outer shell 321 when driven by the external power source. The outer shell 321 is removed from a distal end of the drive shaft 320 to expose the inner gear 322 so that the inner gear may engage the drive mechanism. As would be understood by those of skill in the art, the modular device 110 may further include a slip clutch and a cable which connects to the drive shaft 320 or other suitable drive mechanism to move modular device 110 along the guide track 120 as the drive shaft 320 is rotated.

Those skilled in the art will understand that the described exemplary embodiments of the invention may be altered without departing from the teaching of the invention, e.g., by replacing the spring actuation of the stapler or the linear transducer actuators described by pneumatically actuated mechanisms. Thus, it is to be understood that these embodiments have been described in an exemplary manner and are not intended to limit the scope of this invention which is intended to covers all modifications and variations of this invention that come within the scope of the appended claims and their equivalents.

What is claimed is:

1. A modular device for tissue resection, comprising:
   a housing including a guide track receiving lumen extending therethrough;
   a motor mounted within the housing, the motor being selectively engageable with and rotatable about a guide track received within the guide track receiving lumen to move the modular device therealong;
   a tissue receiving chamber formed within the housing;
   a grabbing mechanism drawing a selected portion of tissue into the tissue receiving chamber; and
   a resection mechanism resecting the selected portion of tissue.

2. The system of claim 1, further comprising a stapling mechanism stapling a portion of tissue adjacent to the selected portion of tissue.

3. The system of claim 1, wherein the housing includes a window moveable between an open position in which the tissue receiving chamber is exposed to an exterior of the housing and a closed position in which the tissue receiving chamber is substantially closed.

4. The system of claim 1, wherein the motor is an electric motor including a sleeve armature extending around the guide track receiving lumen.

5. The device of claim 1, wherein the grabbing mechanism includes opposable arms which may be extended to grasp the selected portion of tissue and retracted to draw the selected portion of tissue into the tissue receiving chamber.

6. The device of claim 1, wherein the grabbing mechanism includes a vacuum port for supplying negative pressure to draw the selected portion of tissue into the tissue receiving chamber.

7. The device of claim 1, wherein the motor is coupled to at least one roller gear moveable between an engagement position in which the at least one roller gear is positioned adjacent to the guide track receiving lumen to engage a guide track received therein and a retracted position in which the roller gear is separated from the guide track receiving lumen.

8. The device of claim 7, wherein the at least one roller gear includes a first set of roller gears positioned adjacent to a proximal end of the guide track receiving lumen and a second set of roller gears positioned adjacent to a distal end of the guide track receiving lumen.

* * * * *